(12) United States Patent
Yvert et al.

(10) Patent No.: US 9,327,242 B2
(45) Date of Patent: May 3, 2016

(54) METHOD FOR HIGH-THROUGHPUT SCREENING OF DROPS BY OSMOTIC EXCHANGE AND DENSITY VARIATION

(75) Inventors: Gaël Yvert, Saint Genis Laval (FR); Jérôme Bibette, Paris (FR); Jean-Marie Baudry, Paris (FR); Laurent Boitard, Paris (FR); Nicolas Bremond, Paris (FR); Denis Cottinet, Paris (FR)

(73) Assignees: CENTRE NATIONAL DE LA RECHERCHE SCIENTIFIQUE (C.N.R.S.), Paris (FR); UNIVERSITE PIERRE ET MARIE CURIE (PARIS 6), Paris (FR); ECOLE NORMALE SUPERIEURE DE LYON, Lyons (FR); UNIVERSITE PARIS DIDEROT—PARIS 7, Paris (FR)

( * ) Notice: Subject to any disclaimer, the term of this patent is extended or adjusted under 35 U.S.C. 154(b) by 306 days.

(21) Appl. No.: 14/006,347

(22) PCT Filed: Mar. 21, 2012

(86) PCT No.: PCT/EP2012/055031
§ 371 (c)(1),
(2), (4) Date: Nov. 27, 2013

(87) PCT Pub. No.: WO2012/126959
PCT Pub. Date: Sep. 27, 2012

(65) Prior Publication Data
US 2014/0069865 A1    Mar. 13, 2014

(30) Foreign Application Priority Data
Mar. 22, 2011    (FR) ...................................... 11 52352

(51) Int. Cl.
*B01D 61/00*    (2006.01)
*G01N 15/04*    (2006.01)
(Continued)

(52) U.S. Cl.
CPC .......... *B01D 61/002* (2013.01); *B01D 19/0036* (2013.01); *B01D 61/38* (2013.01); *C12N 1/00* (2013.01); *G01N 15/0255* (2013.01); *G01N 15/04* (2013.01); *G01N 2015/1081* (2013.01)

(58) Field of Classification Search
None
See application file for complete search history.

(56) References Cited

U.S. PATENT DOCUMENTS 4,649,109 A    3/1987 Perlman

FOREIGN PATENT DOCUMENTS

EP    0 694327 A2    1/1996
WO    WO2009134395 A2    11/2009

OTHER PUBLICATIONS

International Preliminary Examination Report and Written Opinion; PCT/EP2012/055031; issued Jul. 25, 2012.
(Continued)

*Primary Examiner* — Krishnan S Menon
(74) *Attorney, Agent, or Firm* — Hunton & Williams LLP

(57) ABSTRACT

This method comprises bringing drops to be separated into contact with an interface (40) suitable for allowing an osmotic equilibrium between the content of each drop to be separated. The method comprises an osmotic flow between the drops (20A) of the first group of drops through the interface (40) in order to modify the density of each drop (20A) of the first group of drops and the separation of the drops (20A, 20B) according to the density thereof or a combination of the density and the volume in order to isolate the drops (20A) of the first group of drops from the drops (20B) of a second group of drops.

20 Claims, 8 Drawing Sheets

(51) Int. Cl.
*B01D 19/00* (2006.01)
*C12N 1/00* (2006.01)
*G01N 15/02* (2006.01)
*B01D 61/38* (2006.01)
*G01N 15/10* (2006.01)

(56) References Cited

OTHER PUBLICATIONS

Joensson, Haakan N.; "Droplet Size Based Separation by Deterministic Lateral Displacement—Separating Droplets by Cell-induced Shrinking"; *Lab Chip*, 11: 1305-1310 (2011).

METHOD FOR HIGH-THROUGHPUT SCREENING OF DROPS BY OSMOTIC EXCHANGE AND DENSITY VARIATION

CROSS-REFERENCE TO RELATED APPLICATIONS

This application is the U.S. National Phase of International Application No. PCT/EP2012/055031, filed Mar. 21, 2013, which claims priority to French Application No. FR 1152352, filed Mar. 22, 2011. The contents of each are hereby incorporated by reference in their entireties.

SUMMARY OF THE INVENTION

The present invention relates in part to a method for selecting at least one first group of drops (20A) from among a plurality of drops (20) present in a continuous phase (24), the method comprising the following steps:
bringing drops (20) to be separated into contact with an interface (40) suitable for allowing an osmotic equilibrium between the content of each drop (20) to be separated;
osmotic flow between the drops (20A) of a first group of drops and the interface (40) in order to modify the volume of each drop (20A) of the first group of drops, characterized in that the osmotic flow step causes a significant variation in the density of each drop (20A) of the first group of drops; and
separating the drops (20A, 20B) according to the density thereof or according to a combination of the density and the volume to isolate the drops (20A) of the first group of drops from the drops (20B) of a second group of drops.

DETAILED DESCRIPTION OF THE INVENTION

The present invention relates to a method for selecting at least one first group of drops from among a plurality of drops present in a liquid medium, the method comprising the following steps:
bringing drops to be separated into contact with an interface suitable for allowing an osmotic equilibrium between the content of each drop to be separated;
osmotic flow between the drops of a first group of drops and the interface in order to modify the volume of each drop of the first group of drops.

Such a method is for example intended to screen very large libraries of molecules of biological interest that are distributed in emulsion drops. In particular, the method is intended to select drops comprising a particular product from among all of the drops, that product being able to result from a chemical or biological reaction, in particular done using a host cell.

To test in parallel the activity or the properties of the large number of variants of chemical or biological micro-reactors, it is known to distribute the micro-reactors in drops of an emulsion, then to conduct a chemical or biological reaction in each of the micro-reactors.

It is then necessary to separate the drops according to the product they contain, in particular to evaluate and isolate the reaction conditions and the micro-reactors having led to a significant reaction.

This technique is for example applicable in diagnostics, or in gene expression. In the latter case, it is known to produce banks of coding genes, for example for variants of an enzyme, then to place each of the genes obtained in a host organism. Then, each host organism is positioned in a separate drop in order to determine whether that drop has an activity.

In one particular case, each gene is received in a yeast that is placed in a particular drop. The drop contains a nutritional medium and is placed under conditions capable of allowing biological growth. Some yeasts are then capable of significant growth.

To isolate the drops in which significant growth has occurred, it is known to place selective fluorescent markers that are active when the drop has undergone a significant reaction.

Then, the drops are sorted manually or using automatic sorting machines to separate those which reacted, for example, through microfluidic or flow cytometry techniques.

Such techniques are relatively complex and expensive. They only make it possible to discriminate small samples, since the maximum sort that can be obtained is approximately from 1,000 to 10,000 drops per second.

Subsequently, when the starting sample is very large, such techniques are insufficient or too lengthy to implement.

The same problem of separation arises when these screening techniques are used in the field of diagnostics, in the field of the detection of very diluted molecules, or when a large number of test molecules must be tested simultaneously with a same reagent.

As before, it is necessary to separate the drops at a high throughput, failing which the test is too tedious to carry out.

To offset these problems, known from the article "Droplet Size Based Separation by Deterministic Lateral Displacement", published in the review "Lab on a Chip" on Feb. 14, 2011, is a method of the aforementioned type in which the volume of certain drops to be separated is modified by osmotic flow. The volume variation of the drops is very low.

The drops are then separated based on their volume by causing them to flow horizontally through a support provided with spurs. The density of the drops is not involved in the separation and remains substantially constant. Nevertheless, the separating method is tedious to carry out and is not very effective.

One aim of the invention is therefore to have a method for separating a particular group of drops from among a large number of drops that is easy and fast to carry out, while allowing a quick recovery of the screened drops.

Another aim of the invention is to have a method that makes it possible to screen, at a high throughput and in a manner that is easy to carry out, properties that are difficult to access today, such as the metabolism of a microorganism.

To that end, the invention relates to a method of the aforementioned type, characterized in that the osmotic flow step causes a significant variation in the density of each drop of the first group of drops; the method including the following step:
separating the drops according to the density thereof or according to a combination of the density and the volume to isolate the drops of the first group of drops from the drops of a second group of drops.

The method according to the invention may comprise one or more of the following features, considered alone or according to any technically possible combination:
the drops to be separated initially have a relatively monodisperse density, the density variation of the drops of the first group of drops after the osmotic flow step being greater than the initial polydispersity of the densities of the drops to be separated;
the density variation of the drops of the second group of drops after the osmotic flow step is lower than the initial polydispersity of the densities of the drops to be separated;
the drops to be separated contain a non-soluble component in the continuous phase initially representing more than 5 wt % of the mass of each drop to be separated;

the non-soluble component is a polymer with a molar mass greater than 10,000 g/mol;

the interface is formed by at least one other drop to be separated, advantageously by multiple drops to be separated placed in contact with each drop to be separated;

at least one other drop to be separated, advantageously multiple other drops to be separated, have an inverse density variation relative to the density variation of the drops of the first group of drops during the osmotic exchange;

the interface is delimited by a planar surface suitable for allowing an osmotic equilibrium between the content of each drop to be separated, the drops to be separated being placed on the planar surface;

the interface is delimited by a semi-permeable membrane, the drops to be separated being positioned in contact with the membrane;

the significant density variation between the initial density of each drop of the first group of drops before osmotic exchange and the final density of each drop of the first group of drops after osmotic exchange is greater than 12%, in particular greater than 25%;

the number of drops to be separated is greater than $10^6$, the ratio of the number of drops of the first group of drops to the total number of drops to be separated being less than 1/10,000;

the separating step includes placing the drops in a liquid medium with a density that is different from at least one among the density of each of the drops of the first group of drops and among the density of each of the drops of the second group of drops, the method comprising the advantageously spontaneous formation of at least two layers of drops, a first layer comprising primarily drops from the first group of drops, the second layer comprising primarily drops from the second group of drops;

the separating step includes the centrifugation of the medium containing the drops;

the method comprises the addition of an additive in the liquid medium containing the drops to vary the density of the liquid medium, the addition of the additive being done before the separating step, in particular before the osmotic flow step, or during the separating step;

the separating step includes varying the temperature of the liquid medium so as to differentially vary the density of the liquid medium, the density of the drops of the first group of drops and the density of the drops of the second group of drops;

before the step for bringing into contact, it includes the selective reaction in certain drops to be separated of at least one component contained in a plurality of drops to be separated, to form the drops of the first group of drops;

the reaction is a chemical reaction or a biological reaction;

the drops to be separated initially contain a same reactive agent, each drop to be separated containing a distinct reagent, the reactive agent being suitable for causing the reagent to react;

the drops to be separated initially contain a same reagent, each drop to be separated containing a distinct reactive agent, the reactive agent being capable of causing the reagent to react.

The invention will be better understood upon reading the following description, provided solely as an example, and done in reference to the appended drawings, in which.

Figure 1:
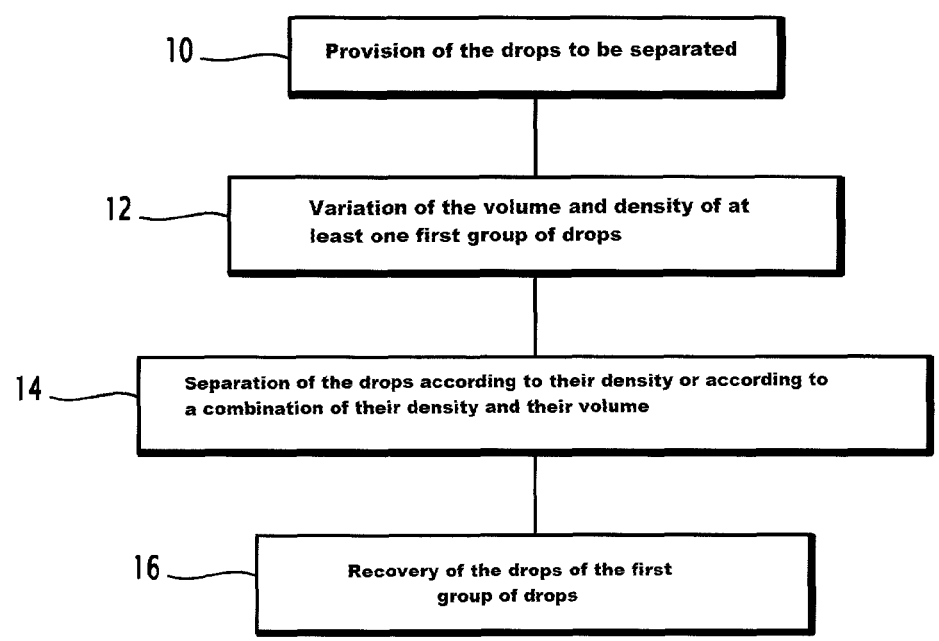
FIG. 1 is a block diagram of a first method according to the invention.

The main steps of a first example of a method according to the invention are diagrammatically shown in FIG. 1.

This method comprises a step 10 for providing a multitude of drops to be separated, a step 12 for varying the volume of at least a first group of drops to be separated among the drops to be separated, then a step 14 for separating the drops based on their density or in combination with the volume.

The method optionally comprises a step 16 for recovering the drops of the first group of drops.

Figure 2:
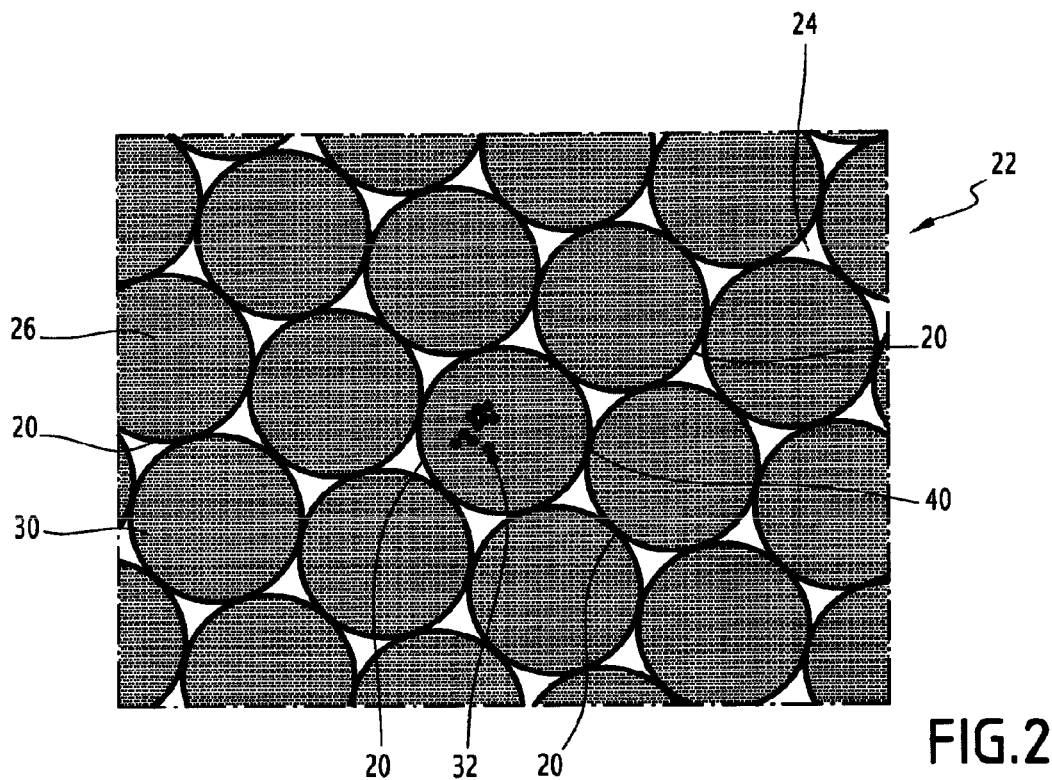
FIG. 2 is a view of a plurality of drops to be separated by a first method according to the invention, at the beginning of implementation of the method.

As illustrated by FIG. 2, the drops 20 to be separated are initially provided in the form of a three-dimensional emulsion 22 of drops dispersed in a continuous medium 24.

The emulsion is for example an emulsion of water drops 20 dispersed in an oily continuous phase 24. Alternatively, the drops 20 are drops of an oily/organic phase dispersed in an aqueous continuous phase 24. In any case, the two fluids respectively forming the continuous phase 24 and the drops 20 are substantially immiscible.

The emulsion 22 is a concentrated emulsion of drops. "Concentrated emulsion" means that the dispersed phase constituting the drops 20 represents more than 60% by volume of the volume of the emulsion 22.

The size of the drops is for example from 5 μm to 500 μm. The number of drops 20 in the emulsion 22 is greater than $10^{10}$, and is in particular greater than $10^{12}$.

The drops 20 initially provided are relatively monodisperse.

"Relatively monodisperse" means that the polydispersity of the drops as measured by small-angle scattering or by optical measurements is less than 15%.

This monodispersity is for example measured using the following optical measuring method.

The drops are placed in a chamber measuring 1 cm² and 40 μm thick. Images of the emulsion are taken using a camera and analyzed to measure the size of each drop, thereby making it possible to access the size distribution.

The drops 20 all comprise at least one liquid phase 30 shared by all of the drops. Certain drops 20 include at least one component 32 that is initially different for each drop 20.

The emulsion 22 is for example made using microfluidic techniques, for example comprising multiplexed microfluidic chips, or by mass emulsification techniques through membranes.

In one advantageous embodiment, each drop 20 constitutes a chemical or biological micro-reactor. Thus, each drop 20 initially contains at least one starting reagent intended to react, and at least one reactive agent, intended to cause the starting reagent to react to transform it into at least one final product.

The drop 20 further optionally comprises at least one agent suitable for causing the conditions of the reaction of the starting product to vary with the reactive agent.

In a first example, the starting reagent varies from drop to drop, such that different starting reagents are subject to the same reactive agent to determine whether the starting reagent is suitable for reacting with the reactive agent in order to obtain the final product.

In this case, the starting reagents are for example different chemical components suitable for reacting with the reactive agent.

Alternatively, the starting reagent is shared by the different drops 20 and the drops 20 comprise different reactive agents to determine whether each reactive agent is suitable for reacting with the same starting reagent to form a final product.

In that case, the reactive agents are for example homogenous or heterogeneous catalysts, of different natures depending on the drops 20, to make it possible to test the activity of those catalysts with respect to a same starting reagent.

In one alternative, the reactive agent is for example a microorganism, such as a bacteria or yeast or isolated cells of a superior organism. The different cells present in the different drops 20 have distinct characteristics, for example distinct genes.

In still another alternative, each drop contains the same starting reagent, the same reactive agent, and at least one different additional agent.

In still another alternative, only certain drops 20 contain a starting reagent suitable for reacting with a given reactive agent.

In that case, the method according to the invention makes it possible to isolate products that may be very diluted in a given continuous medium.

In the first step of the method, the concentrated emulsion 22 is for example formed using traditional emulsification techniques or microfluidic techniques.

The obtained drops 20 are relatively monodisperse, as illustrated by FIG. 2. Subsequently, the drops have a relatively monodisperse density.

Then, in the step 12 for varying the volume, each drop 20 to be separated is placed in contact with an interface 40 with the aim of performing osmotic exchange with a continuous medium situated across from the interface 40 that will serve as an "osmotic reference".

Figure 3:
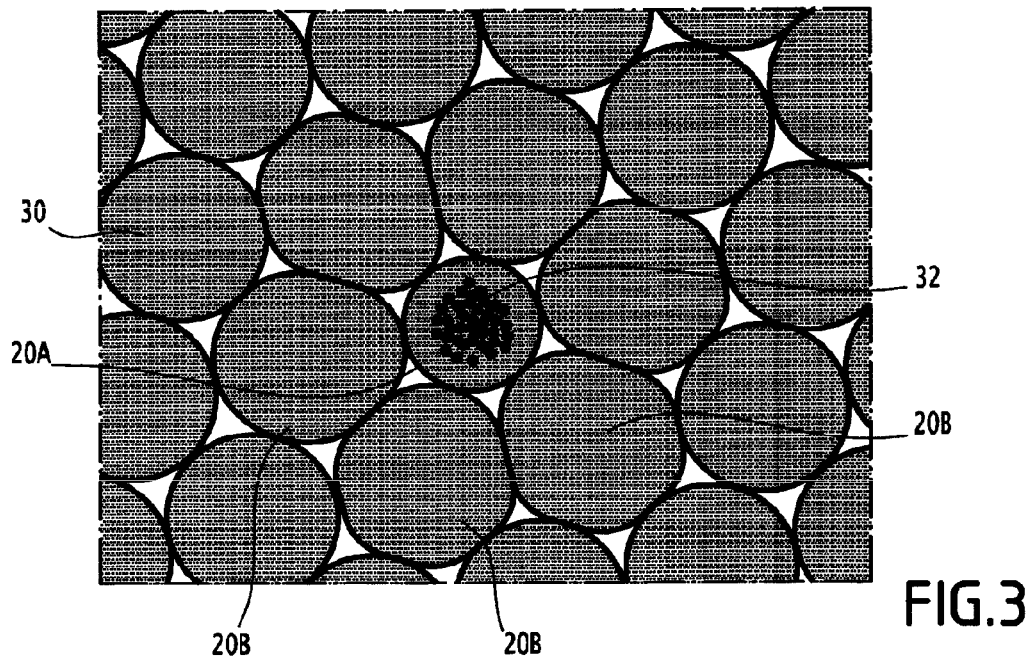
FIG. 3 is a view similar to FIG. 2, after the step for varying the volume of at least one first group of drops.

In the embodiment of FIGS. 2 and 3, each drop 20 to be separated is advantageously placed in contact with at least one adjacent drop 20.

Advantageously, each drop 20 is placed in contact with a plurality of adjacent drops 20 situated all around the drop 20. In particular, the contact is three-dimensional. Thus, the drop 20 is placed in contact with drops 20 substantially in the same plane as the drop 20, and also with at least one drop 20 situated in a plane secant to the aforementioned plane.

Due to their content, at least some drops 20A have a different chemical potential from the adjacent drops 20B.

On the contrary, no significant reaction having occurred in the drops 20B, their chemical potential of the solvent remains substantially constant. The drops 20B for example contain exclusively solvent, or contain a reagent not having reacted with the reactive agent.

Figure 5:
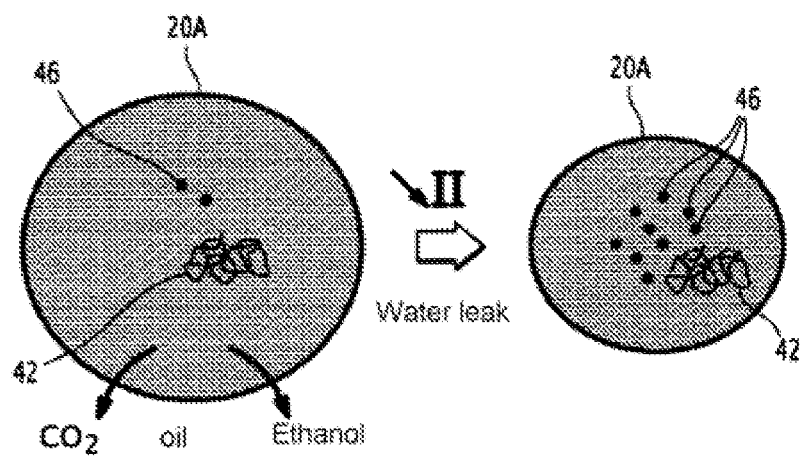
FIG. 5 is a diagrammatic view illustrating a first example of application of the method according to the invention.

In particular, in the example illustrated by FIG. 5, when the drops 20A are micro-reactors, the reaction of the starting reagent contained in at least one drop 20A can create a final product that is at least partially soluble in the continuous phase 24.

The final product then leaves the drop 20A, which causes a flow of liquid phase 30 outside the drop 20A to rebalance the chemical potentials with the adjacent drops 20B.

Figure 9:
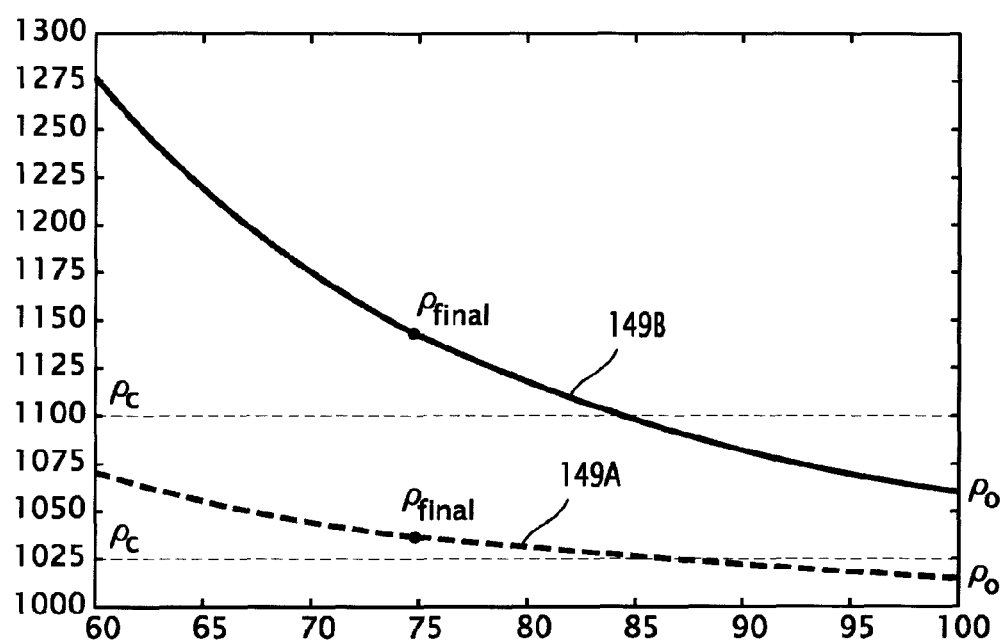
FIG. 9 illustrates the variation of the density according to the volume of drops during a spontaneous separating step of the drops of a first group of drops and a second group of drops.

In that case, as shown diagrammatically in FIG. 5, the size of each drop 20A of a first group of drops decreases due to the high consumption of one of the reagents initially contained in the drop 20A by the reactive agents 46 present in the drop 20A, which amounts, as shown in FIG. 9, to an increase in the density that is even more significant when the drops contain a polymer that is not soluble in the continuous phase.

Figure 4:
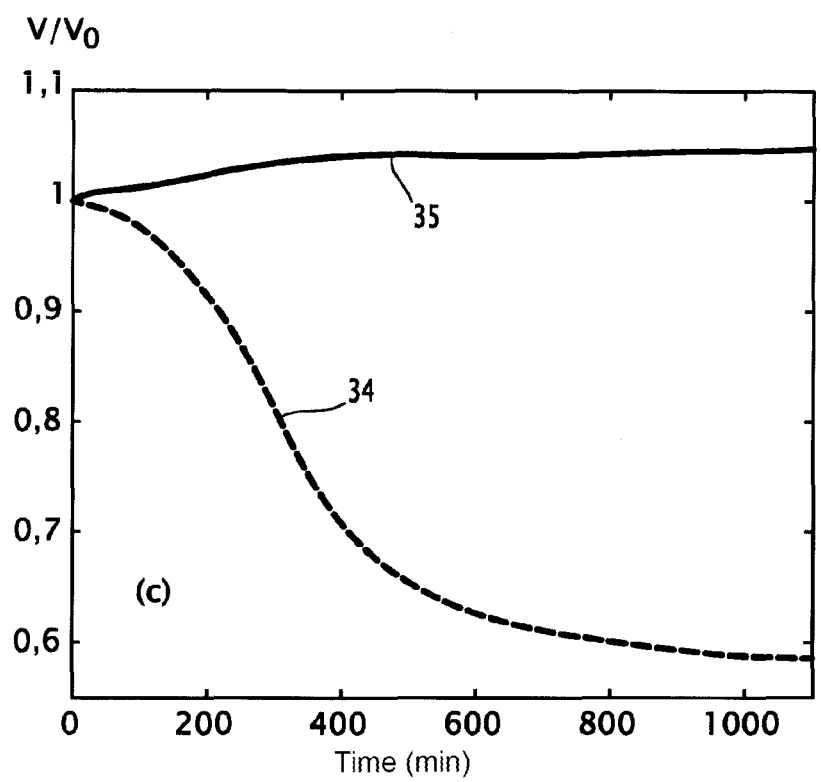
FIG. 4 is a curve of the relative variation of the volume of a first group of drops and a second group of drops, during implementation of the method according to the invention.

The chemical potential of the solvent in the drop 20A therefore decreases, causing a leak of the solvent toward the adjacent drops 20B and a corresponding decrease in the volume of each drop 20A of the first group of drops, as illustrated by the curve 34 in FIG. 4.

As illustrated by the curve 35 in FIG. 4, the volume of each adjacent drop 20B increases slightly, but less significantly in proportion than the decrease of the volume of the drops 20A and according to the ratio of the drops 20A and 20B.

Figure 6:
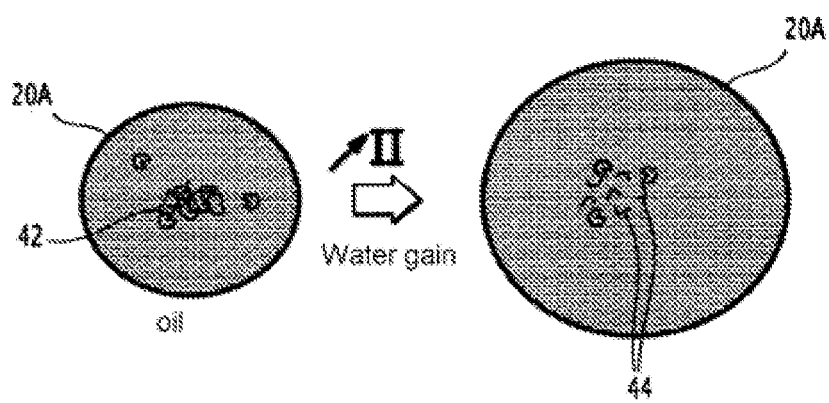
FIG. 6 is a diagrammatic view similar to FIG. 5 illustrating a second example of application of the method according to the invention.

Alternatively, in the case illustrated by FIG. 6 where the number of species 44 present in the drop 20A increases due to the reaction produced therein, the chemical potential of the solvent in the drop 20A increases in an associated manner. The drop 20A then increases in volume by capturing, by osmotic exchange through the interface 40, liquid phase 30 present in the adjacent drops 20B, which rebalances the chemical potentials and amounts to a decrease in the density of the drops 20A.

Thus, in this case, the volume of the drops 20A increases and the volume of the adjacent drops 20B, in which no action has occurred, decreases in a corresponding manner.

The step for varying the volume therefore comprises varying the volume of at least one first group of drops 20A in which a variation of chemical potential has occurred to increase or decrease the volume of said drops 20A, and the inverse variation of the volume of the adjacent drops 20B for which no significant variation in chemical potential has occurred.

Thus, the volume variation (decrease or increase) of the drops 20A of the first group of drops is greater than the polydispersity. In particular, this variation is greater than 20% and is in particular greater than 30%, or even greater than 40%, as illustrated by FIG. 4.

In light of the dilution effect between the different drops 20B adjacent to the drop 20A, the volume variation of each drop 20B is less than 40%, in particular less than 10%. Furthermore, a large number of drops 20 keep a substantially constant volume. In one alternative, the volume variation of the drops 20B is greater than 40%, but remains in the direction opposite the volume variation of the drops 20A.

According to the invention, the volume variation of the drops 20A leads to a significant variation of the density of the drops 20A. Thus, the significant density variation between the initial density of each drop of the first group of drops 20A before osmotic exchange and the final density of each drop of the first group of drops 20A after osmotic exchange is greater than 12%, in particular greater than 25%.

The density variation is even more significant as the initial mass contained in each drop 20 is higher.

In the case where the drops 20 are micro-reactors, this variation makes it possible to identify the micro-reactors in which a significant reaction has occurred, which produced a significant variation in the density.

As seen above, the variation of chemical potential results either from the consumption of the starting reagent to form a final product that is soluble in the continuous phase 24 and that leaves the drop 20A, or from the obtainment of a higher number of species in the drop 20A, or more generally from other physicochemical phenomena able to affect the chemical potential.

In the case where the drop 20 contains a microorganism 46 (see FIG. 5), the starting reagent may be a medium suitable for being consumed by the microorganism to ensure its development, the microorganism producing components soluble in the continuous phase 24.

In particular, the starting product is advantageously a sugar, which is consumed by the microorganism to ensure the growth thereof. The consumption of the sugar forms carbon dioxide and at least one alcohol that diffuse in the continuous phase, causing a decrease in the chemical potential of the drop 20A.

Alternatively, when the starting product 42 is broken down into a plurality of species 44, in particular in the context of the protein lysis reaction, the residues 44 remaining in the drop 20A, the chemical potential of the solvent in the drop 20A increases, which causes a corresponding increase in volume and consequently a decrease in density.

In the separating step 14, the drops 20A of the first group of drops, which have undergone a significant density variation, are separated from the other drops 20B. Thus, only the drops having undergone a significant variation in their volume and therefore their density will be separated.

Preferably, the separation occurs spontaneously, in particular under the effect of gravity.

According to the invention, the drops 20A, 20B are separated according to their density, which is directly correlated to their volume variation.

To that end, the drops 20 are advantageously charged with a component that is not soluble in the continuous phase, such as a polymer 42 (visible in FIG. 5) with a high enough molar mass not to affect the osmotic pressure. The molar mass of the polymer 42 is for example greater than 10,000 g/mol. The polymer advantageously represents more than 5 wt % of the drop.

In this case, and as illustrated in curve 149B of FIG. 9, the density of the drop 20 varies significantly during its decrease or increase in size, in particular by more than 40%.

The effect of the non-soluble component on the density variation is illustrated by FIG. 9, which shows the density variation 149A observed in the absence of a non-soluble component and the same variation 149B in the presence of the non-soluble component.

The drops 20A that undergo a decrease in size have a density that increases gradually, such that their buoyancy in the continuous phase decreases.

The drops 20A will therefore be distributed in the continuous phase according to their own density relative to the density of the continuous phase.

Figures 7, 8:
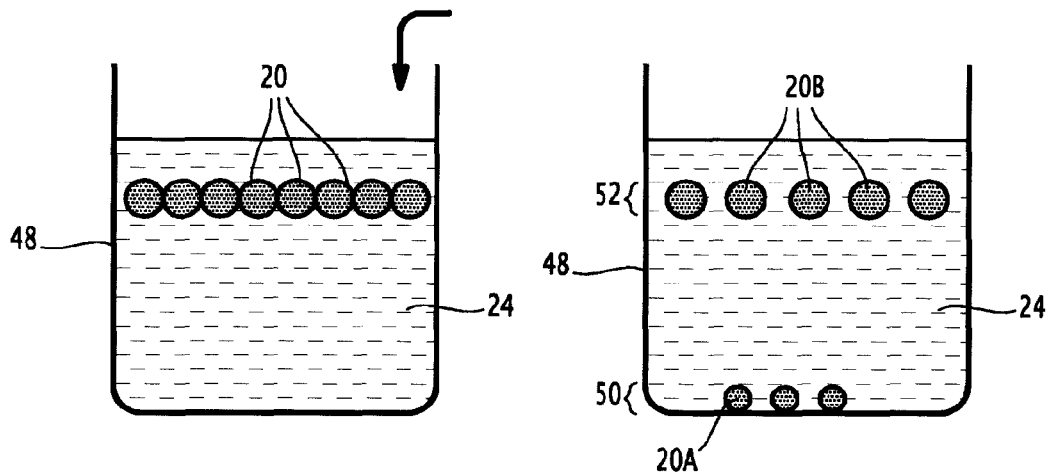
FIG. 7 is a diagrammatic view of a first embodiment of the step for separating the drops based on their density in the method according to the invention.
FIG. 8 is a view similar to FIG. 7, after the separation.

In a method illustrated by FIGS. 7 and 8, the volume variation of the drops 20A is associated with a density variation between an initial density $\rho_o$ illustrated in FIG. 9 and a final density $\rho_f$. In that case, the density $\rho_c$ of the continuous phase 24 is chosen to be comprised between the initial density $\rho_o$ of the drops 20 and the final density $\rho_f$ of the drops 20A of the first group of drops.

Figure 10:
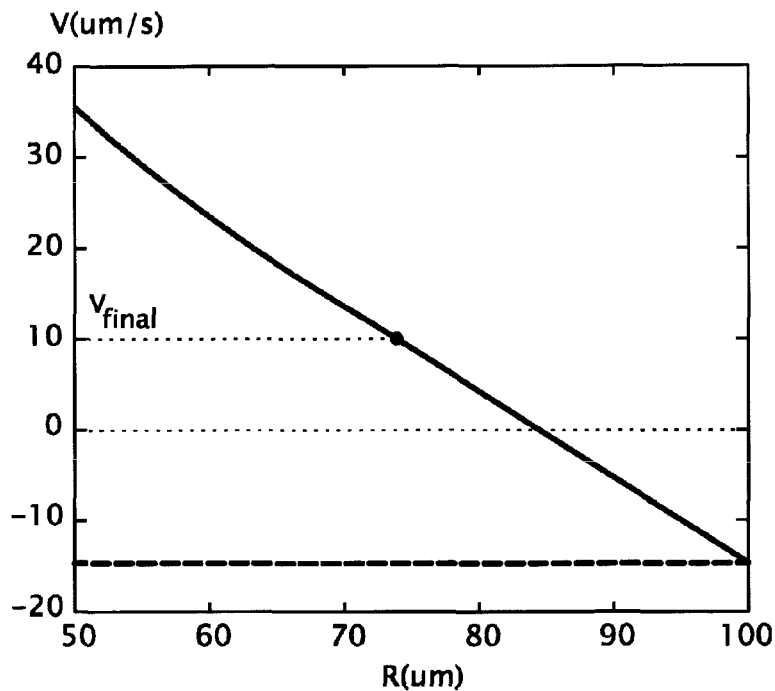
FIG. 10 is a view illustrating the sedimentation or creaming speed of a drop in the course of its volume reduction (densification) in a given liquid medium.

The density of the drops 20B of the second group of drops remaining substantially constant, due to the low volume variation of those drops, it is possible to easily and spontaneously separate drops 20A of the first group of drops from the other drops 20B. This is illustrated by the sedimentation speed $v_{final}$ illustrated in FIG. 10.

In the example illustrated by FIGS. 7 and 8, the drops 20B have an initial density substantially equal to or lower than the density of the continuous phase.

The volume of the drops 20A of the first group of drops will decrease in step 12. Their density therefore increases and exceeds the density of the continuous phase.

The drops 20A of the first group of drops then undergo sedimentation and may be recovered in the form of a layer 50, as is illustrated by FIG. 8. A layer 52 of drops 20B remains in suspension.

Alternatively, an additive is added in the continuous phase 24, for example at the end of the reaction to modify the density $\rho_c$ of the continuous phase 24 and thus place that density $\rho_c$ between the density of the drops 20A of the first group of drops and the density of the drops 20B of the second group of drops.

In all cases, the separation of drops 20A, 20B may be accelerated by centrifugation.

Figure 11:
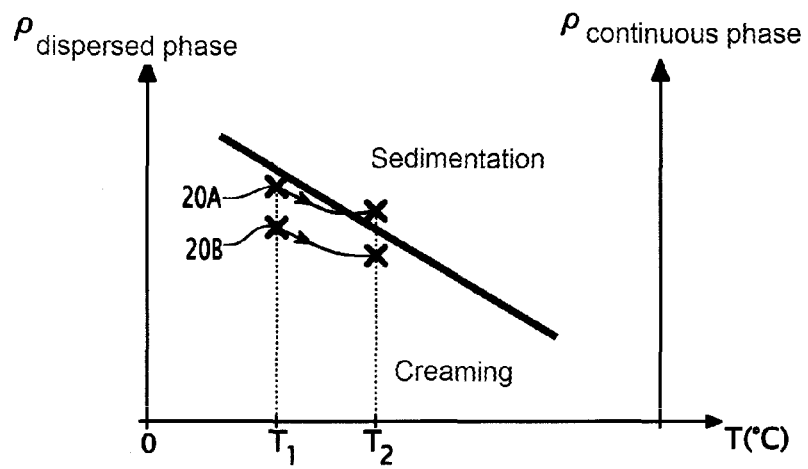
FIG. 11 is a curve showing the density according to the temperature to illustrate a method for separating the first group of drops by temperature variation.

In another alternative, the temperature of the emulsion 22 is modified after the volume variation of the drops 20A of the first group of drops. The density of the continuous phase 24, the density of the drops 20A of the first group of drops and the density of drops 20B of the second group of drops vary differentially according to the temperature (FIG. 11), which causes the spontaneous separation of the drops 20A, 20B according to their density (as for FIG. 8).

As previously described, different layers 50, 52 (FIG. 8) respectively containing the drops 20A of the first group of drops and the drops 20B of the second group of drops are then formed.

Once the drops 20A of the first group of drops are separated from the drops 20B of the second group of drops, they are recovered in step 16. This makes it possible to easily and quickly isolate the drops 20A that have undergone a significant variation in chemical potential, from among a very large number of initial drops.

The content of the drops 20A is then recovered and/or analyzed, if necessary.

Figure 12:
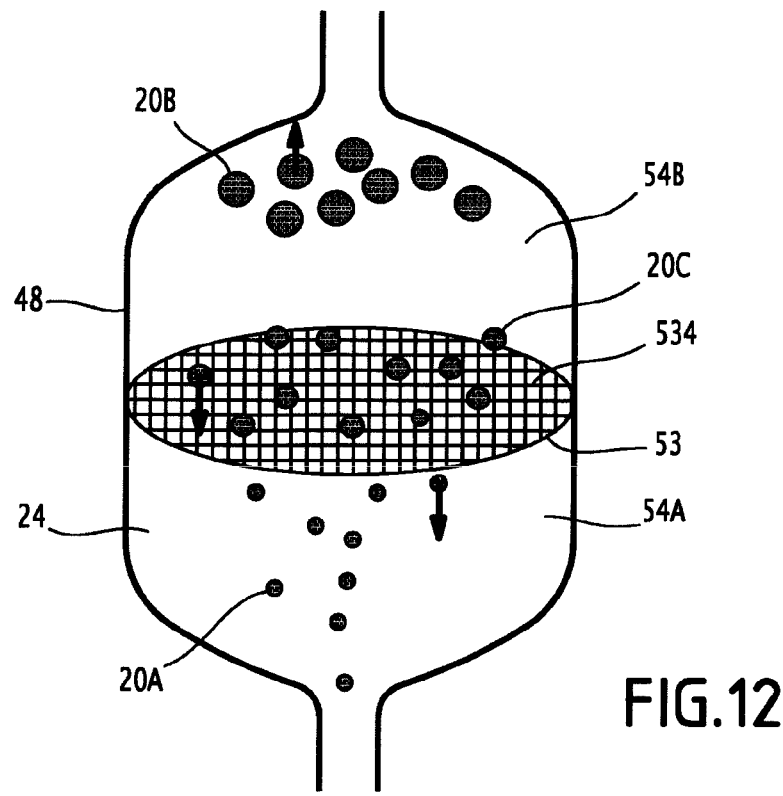
FIG. 12 is a diagrammatic partial cross-sectional view of an alternative step for separating the drops using the method according to the invention.

In one alternative, shown in FIG. 12, the drops 20A, 20B obtained after volume variation are placed in a continuous phase 24 with a density greater than that of the drops 20B and lower than that of the drops 20A.

The continuous phase 24 is received in a container 48 provided with an intermediate filter 53 submerged in the continuous phase 24. The filter 53 defines passage openings 53A with a maximum dimension smaller than a critical dimension of the drops 20A.

The drops 20A, 20B are then placed in the upper region 54B of the container situated above the filter 53. The drops 20B spontaneously rise under the effect of gravity. The drops 20A settle toward the filter 53. However, only the drops 20A having undergone a significant volume reduction pass through the openings 53A of the filter 53 to reach the lower region 54B of the container 48 situated below the filter 53. The drops 20A are then recovered, as described above. In one alternative, a group of drops 20C having undergone an insufficient volume variation remains retained on the filter.

As an example, a 50 µm filter may be used to separate the drops from an emulsion of drops 20 with a diameter of 70 µm whereof the drops 20A undergo a volume reduction of 90%.

Figure 13:
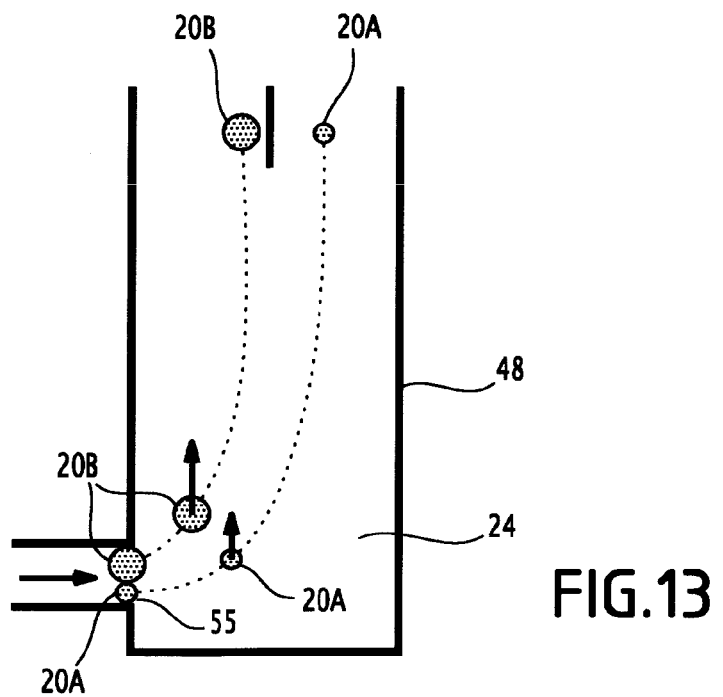
FIG. 13 is a view similar to FIG. 12 of another alternative of a step for separating the drops using the method according to the invention.

In another alternative, illustrated in FIG. 13, the drops 20A, 20B are injected horizontally in the vicinity of the bottom of the container 48 at a given horizontal speed. The container 48 contains a continuous phase 24 with a density that is higher than that of the drops 20A, 20B.

Under the effect of the gravitational field, the drops 20A, 20B are deviated upward and their trajectory curves. The horizontal deviation of the drops will, however, depend on the radius of the drop 20A, 20B. The separation is created by the combination between the density variation and volume variation of the drops 20A, relative to the drops 20B.

Thus, the relatively small drops 20A will be deviated while being relatively horizontally further from the injection opening 55 of the drops, while the larger drops 20B will be deviated while being relatively horizontally closer to the opening 55.

The container 48 advantageously has a shape of revolution around an axis A-A'.

Alternatively, when the density of the continuous phase is chosen at an intermediate value between the drops 20A and the drops 20B, only the drops 20B are deviated upward.

The drops 20A having undergone a volume decrease are deviated downward.

Figure 14:
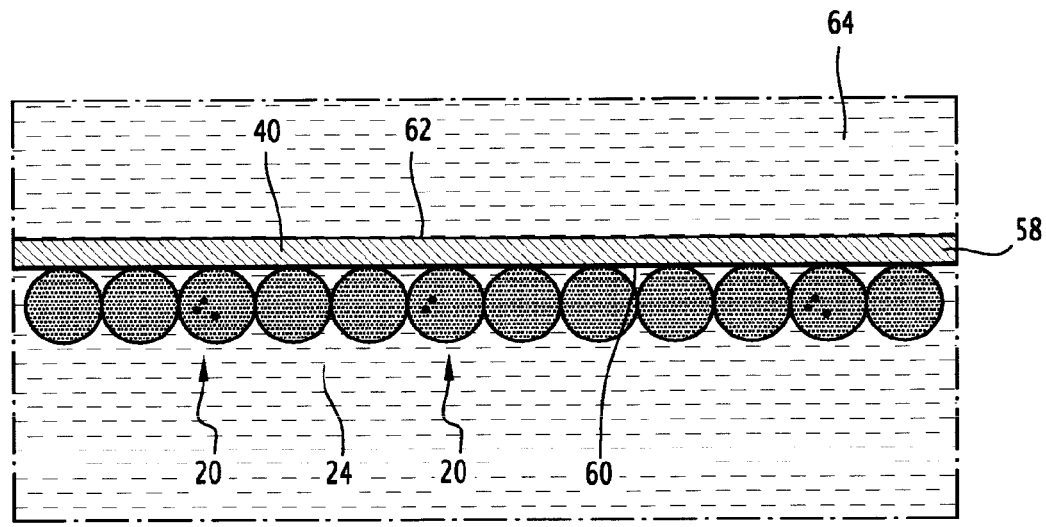
FIG. 14 is a view similar to FIG. 2 for a second method according to the invention.
Figure 15:
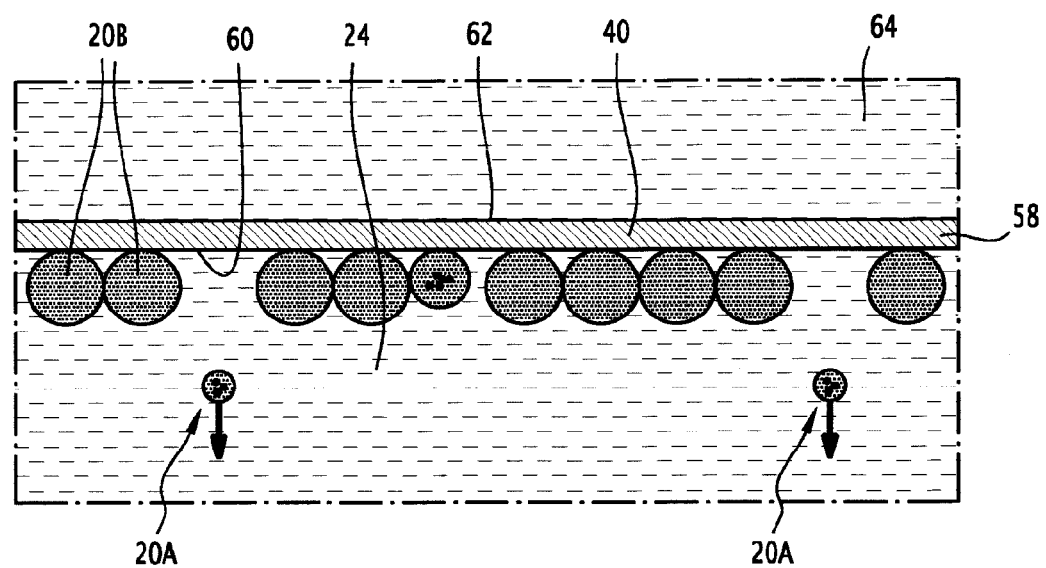
FIG. 15 is a view similar to FIG. 3 for the second method according to the invention.

In a second method according to the invention, shown in FIGS. 14 and 15, the interface 40 is at least partially formed by a semi-permeable membrane 58 allowing the diffusion of chemical components with a low molar mass (below 180 g/mol) and solvent, but preventing the passage of the drops 20.

A single layer of drops 20 to be separated is deposited below the surface 60 of the membrane 58. An opposite surface 62 of the membrane is brought into contact with a fluid 64 of the same nature and same chemical potential as the liquid initially contained in the drops 20.

During the variation in chemical potential of the drops 20A of the first group of drops, part of the liquid phase 30 contained in the drops 20A migrates through the interface 40 toward the fluid 64, which causes an increase in the density of the drops 20A that will settle.

In one alternative (not shown), the variation in chemical potential in the drops 20A causes a migration of the liquid phase 30 contained in the volume 64 through the membrane 60 to inflate the drops 20A of the first group of drops.

Then, the drops 20A of the first group of drops are separated from the other drops 20B in a self-separation step 14 similar to that previously described.

The drops 20A having undergone a significant density variation are then recovered. The content of the drops 20A is then recovered and/or analyzed, if necessary.

In another alternative, the volume variation of the drops 20 is done such that a plurality of classes of drops 20A having undergone a significant density variation after the implementation of the osmotic flow are obtained. The different classes of drops 20A obtained, for example at least two or three classes, are separated according to their density.

Non-limiting examples of embodiments of the invention will now be described.

Example 1

Screening of a Plurality of Yeasts

A plurality of yeasts having different genetic characteristics are initially disposed in an aqueous phase containing a culture medium such as glucose. An emulsion of the aqueous phase in an oil is formed to form a plurality of drops 20, each drop 20 containing at least one yeast.

The different drops 20 each contain yeasts with different characteristics.

The emulsion 22 is concentrated such that each drop 20 is brought into contact with a plurality of adjacent drops 20. The formed drops 20 are monodisperse.

In certain drops 20A of the first group of drops, growth of the yeasts is observed, while in the other drops 20B, no growth is observed or they are empty.

The growth of the yeasts causes the multiplication of microorganisms in the drops 20A of the first group of drops. Increased glucose consumption occurs in the drops 20A, which forms carbon dioxide and ethanol. The ethanol and the carbon dioxide migrate into the continuous phase 24.

An osmotic exchange then occurs between the drops 20B adjacent to the drops 20A to reestablish the chemical potential equilibrium between the drops 20A, 20B.

To that end, liquid phase 30 present in the drops 20A crosses the interface 40 between the drops 20A, 20B and scatters in the adjacent drops.

The volume of the drops 20A decreases significantly, for example by more than 40%, in particular by more than 90%. This amounts, for the drops initially containing at least 6 wt % of polymer, to an increase in the density of 12%, in particular more than 25%. The volume of the adjacent drops increases by less than 10%, in particular less than 2%, with a low density variation, negligible relative to that of the drops 204.

Then, the drops 20A are separated from the other drops 20B using one of the methods described above, and are recovered.

Example 2

Detection of a Very Diluted Pathogenic Agent in a Continuous Phase

A solution in which one wishes to test the presence of pathogenic agents is diluted in a medium that favors the growth of the pathogens. The mixture is then fragmented in an emulsion. Drops containing the pathogenic agents will undergo a size reduction. Knowing the initial volume, the volume of the drops and the number of drops that have densified, it is then possible to access the contamination rate of the sample to be tested, and recover the pathogenic agents to identify them.

Example 3

Screening of the Reaction of a Bank of Chemical Molecules Using a Same Reagent: Search for Inhibitors for a Lysis Enzyme (Protease Type)

A library of drops each containing a potential inhibitor is fused with drops containing the reagents (enzyme+polymer or protein). The drops containing non-inhibiting chemical molecules will inflate due to the increase in the chemical potential associated with the protein lysis (increase in the number of objects in the drop). The drops containing the inhibitors will decrease slightly. The separation of the two types of drops will make it possible collect the inhibitors.

Example 4

Screening of a Series of Heterogeneous or Homogenous Catalysts: Evolution Directed on Enzymes A library of mutants of the enzyme one wishes to improve is formed using the traditional mutagenesis methods. The in vitro compartmentalization method developed by Tawfik et al. to encapsulate a unique gene in each drop is used. Each drop contains a mutated gene, the transcription enzymes to be able to synthesize the enzyme, as well as the reagents on which the enzyme must act. Either the enzyme has a lysis activity, in which case the drops of interest will become inflated, or it has a polymerase activity, in which case the number of species in the drop decreases, which amounts to drops that decrease in volume (densification).

As indicated above, the method according to the invention is advantageously implemented using drops 20 that are substantially immiscible with the continuous phase 24.

In particular, the solubility of the fluid forming the drops 20 in the fluid forming the continuous phase 24 is lower than 0.1 wt % at 25° C.

Likewise, the component that is not soluble in the continuous phase has a solubility advantageously lower than 0.01 wt % in the continuous phase, as measured at 25° C.

The separating method according to the invention therefore allows very effective separation of the drops that are "active" relative to the drops that are not "active".

The activity of the drops amounts to a significant density variation that is advantageously amplified by the presence of the component that is not soluble in the continuous phase in the drops 20, combined with a volume variation associated with a possible activity of the drop 20.

This activity may be a growth activity of microorganisms, but also a metabolic or enzymatic activity. Thus, the method according to the invention does not only make it possible to separate drops in which a number of microorganisms (for example, cells or yeasts) has increased relative to drops not including microorganisms or including fewer microorganisms than the drops that have experienced growth.

The method according to the invention also applies to drops that keep a constant number of microorganisms, but that have different metabolic and/or enzymatic activities. The method according to the invention therefore does not simply apply to cell division, but may apply to enzymatic reactions or PCR. This makes it possible to detect activities amounting to an increase in the size of the drop and a decrease in the density.

The invention claimed is:

1. A method for selecting a first group of drops from among an initial plurality of drops to be separated present in a continuous phase, the method comprising:
   bringing the plurality of drops into contact with an interface suitable for allowing an osmotic equilibrium between the content of each drop to be separated;
   implementing osmotic flow between the drops of a first group of drops and the interface in order to modify the volume of each drop of the first group of drops, wherein the osmotic flow step causes a significant variation in the density of each drop of the first group of drops; and
   separating the drops of the first group of drops from the drops of a second groups of drops according to the density thereof or according to a combination of the density and the volume thereof.

2. The method of claim 1, wherein the interface is formed by at least one other drop to be separated placed in contact with each drop to be separated.

3. The method of claim 2, wherein, during the osmotic flow step, at least one other drop to be separated has an inverse density variation relative to the density variation of the drops of the first group of drops.

4. The method of claim 1, wherein the interface is delimited by a planar surface suitable for allowing an osmotic equilibrium between the content of each drop to be separated, the drops to be separated being placed on the planar surface.

5. The method of claim 4, wherein the interface is delimited by a semi-permeable membrane, the drops to be separated being positioned in contact with the membrane.

6. The method of claim 1, wherein the density variation between the initial density of each drop of the first group of drops before the osmotic flow step and the final density of each drop of the first group of drops after the osmotic flow step is greater than 12%.

7. The method of claim 1, wherein the number of drops to be separated is greater than $10^6$ and the ratio of the number of drops of the first group of drops to the total number of drops to be separated is lower than 1/10,000.

8. The method of claim 1, wherein the separating step includes placing the drops in a liquid medium with a density that is different from at least one among the density of each of the drops of the first group of drops and among the density of each of the drops of the second group of drops, the method comprising the spontaneous formation of at least two layers of drops, a first layer comprising primarily drops from the first group of drops, and a second layer comprising primarily drops from the second group of drops.

9. The method of claim 8, wherein the separating step includes the centrifugation of the medium containing the drops.

10. The method of claim 8, wherein, before or during the separating step, an additive is added to the liquid medium containing the initial plurality of drops to vary the density of the liquid medium.

11. The method of claim 8, wherein the separating step includes varying the temperature of the liquid medium so as to differentially vary the density of the liquid medium, the density of the drops of the first group of drops and the density of the drops of the second group of drops.

12. The method of claim 1, wherein, before the initial plurality of drops to be separated is brought into contact with the interface, a selective reaction of at least one component contained in certain drops of the initial plurality of drops to be separated takes place to form the drops of the first group of drops.

13. The method of claim 12, wherein the reaction is a chemical reaction or a biological reaction.

14. The method of claim 13, wherein each drop to be separated initially contains a distinct reagent but all such drops initially contain the same reactive agent, the reactive agent being suitable for causing the reagent to react.

15. The method of claim 13, wherein each drop to be separated initially contains a distinct reactive agent but all such drops initially contain the same reagent, the reactive agent being capable of causing the reagent to react.

16. The method of claim 1, wherein the drops to be separated contain, within the internal volume of the drop, a component that is not soluble in the continuous phase, the component initially representing more than 5 wt % of the mass of each such drop.

17. The method of claim 1, wherein the fluids forming the continuous phase and the drops are immiscible.

18. The method of claim 6, wherein the density variation between the initial density of each drop of the first group of drops before the osmotic flow step and the final density of each drop of the first group of drops after the osmotic flow step is greater than 25%.

19. The method of claim 10, wherein the addition of the additive is done before the osmotic flow step.

20. The method of claim 16, wherein the component that is not soluble in the continuous phase is a polymer with a molar mass greater than 10,000 g/mol.

* * * * *